US009757448B2

(12) United States Patent
Weiner et al.

(10) Patent No.: US 9,757,448 B2
(45) Date of Patent: Sep. 12, 2017

(54) METHODS OF TREATING CEREBRAL AMYLOID ANGIOPATHY (75) Inventors: Howard Weiner, Brookline, MA (US); Dan Frenkel, Rehovot (IL); Veronica Lifshitz, Tel Aviv (IL)

(73) Assignees: The Brigham and Women's Hospital, Inc., Boston, MA (US); Ramot At Tel Aviv University Ltd., Tel Aviv (IL)

( * ) Notice: Subject to any disclaimer, the term of this patent is extended or adjusted under 35 U.S.C. 154(b) by 1208 days.

(21) Appl. No.: 13/579,817

(22) PCT Filed: Feb. 24, 2011

(86) PCT No.: PCT/US2011/026074
§ 371 (c)(1),
(2), (4) Date: Mar. 29, 2013

(87) PCT Pub. No.: WO2011/106525
PCT Pub. Date: Sep. 1, 2011

(65) Prior Publication Data
US 2013/0183245 A1 Jul. 18, 2013

Related U.S. Application Data (60) Provisional application No. 61/308,678, filed on Feb. 26, 2010.

(51) Int. Cl.
*A61K 39/39* (2006.01)
*A61K 31/739* (2006.01)
*A61K 38/16* (2006.01)
*A61K 45/06* (2006.01)

(52) U.S. Cl.
CPC ............ *A61K 39/39* (2013.01); *A61K 31/739* (2013.01); *A61K 38/164* (2013.01); *A61K 45/06* (2013.01)

(58) Field of Classification Search
CPC ...... A61K 31/739; A61K 45/06; A61K 39/39; A61K 38/164
See application file for complete search history.

(56) References Cited

U.S. PATENT DOCUMENTS

| 5,726,292 | A | 3/1998 | Lowell |
| 5,985,284 | A | 11/1999 | Lowell |
| 6,468,798 | B1 | 10/2002 | Debs et al. |
| 7,524,509 | B2 | 4/2009 | Burt et al. |
| 2001/0053368 | A1 | 12/2001 | Burt et al. |
| 2003/0044425 | A1 | 3/2003 | Burt et al. |
| 2009/0318337 | A1 | 12/2009 | Lowell et al. |

FOREIGN PATENT DOCUMENTS

WO  WO 2011/106525  9/2011

OTHER PUBLICATIONS

Weiner et al., Nature Reviews Immunology 6, 404-416 (2006).*
Van Rooden et al.,Stroke. 2009;40:3022-3027.*
Bornebroek et al; Hereditary Cerebral Hemorrhage with Amyloidosis-Dutch Type (HCHWA-D): I—A Review of Clinical, Radiologic and Genetic Aspects; Brian Pathology; 1996; 6:111-114.
Burgermeister et al; Mechanisms of Cerebrovascular Amyloid Deposition—Lessons from Mouse Models; Ann NY Acad. Sci.; 2000; 903:307-316.
Buttini et al; β-Amyloid Immunotherapy Prevents Synaptic Degeneration in a Mouse Model of Alzheimer's Disease; The Journal of Neuroscience; 2005; 25(40):9096-9101.
Chung et al; Hypoperfusion and Ischemia in Cerebral Amyloid Angiopathy Documented by 99mTc-ECD Brain Perfusion SPECT; J. Nucl. Med.; 2009; 50:1969-1974.
Coffey et al; Brain derived neurotrophic factor induces a rapid upregulation of synaptophysin and tau proteins via the neurotrophin receptor TrkB in rat cerebellar granule cells; Neuroscience Letters; 1997; 227:177-180.
Connor et al; Brain-derived neurotrophic factor is reduced in Alzheimer's disease; Molecular Brain Research; 1997; 49:71-81.
Daly et al; Synaptophysin regulates clathrin-independent endocytosis of synaptic vesicles; PNAS; 2000; 97(11):6120-6125.
El Khoury et al; Ccr2 deficiency impairs microglial accumulation and accelerates progression of Alzheimer-like disease; Nature Medicine; 2007; 13(4):432-438.
Ellis et al; Cerebral amyloid angiopathy in the brains of patients with Alzheimer's disease: The CERAD experience, part XV; Neurology; 1996; 46:1592-1596.
Farfara et al; Neuroprotective and neurotoxic properties of glial cells in the pathogenesis of Alzheimer's disease; J. Cell. Mol. Med. ; 2008; 12(3):762-780.
Farrall et al; Blood-brain barrier: Ageing and microvascular disease-systematic review and meta-analysis; Neurobiology of Aging; 2009; 30:337-352.
Frangione et al; Familial cerebral amyloid angiopathy related to stroke and dementia; Amyloid:J. Protein Folding Disord.; 2001; 8(1):36-42.
Frenkel et al; A Nasal Proteosome Adjuvant Activates Microglia and prevents Amyloid Deposition; Ann Neurol.; 2008; 63(5):591-601.
Frenkel et al; Nasal vaccination with a proteosome-based adjuvant and glatiramer acetate clears β-amyloid in a mouse model of Alzheimer disease; The Journal of Clinical Investigation; 2005; 115(9):2423-2433.
Gomez-Pinilla et al; Voluntary Exercise Induces a BDNF-Mediated Mechanism That Promotes Neuroplasticity; J. Neurophysiol.; 2002; 88:2187-2195.
Grabowski et al; Novel Amyloid Precursor Protein Mutation in an Iowa Family with Dementia and Severe Cerebral Amyloid Angiopathy; Ann. Neurol.; 2001; 49:697-705.
Greenberg et al; Amyloid Angiopathy-Related Vascular Cognitive Impairment; Stroke; 2004; 35(1):2616-2619.
Greenberg et al; The clinical spectrum of cerebral amyloid angiopathy: Presentations without lobar hemorrhage; Neurology; 1993; 43:2073-2079.

(Continued)

Primary Examiner — Michael Hartley
Assistant Examiner — Robert Cabral
(74) Attorney, Agent, or Firm — Fish & Richardson P.C.

(57) ABSTRACT

Methods for treating and reducing risk of cerebral amyloid angiopathy (CAA) using nasal vaccination with a proteosome adjuvant.

11 Claims, 9 Drawing Sheets (56) References Cited

OTHER PUBLICATIONS

Hawkes et al; Selective targeting of perivascular macrophages for clearance of β-amyloid in cerebral amyloid angiopathy ; PNAS; 2009; 106(4):1261-1266.
International Search Report and Written Opinion; Hee, Choi Sung; Nov. 24, 2011; World Intellectual Property Organization (WIPO) (International Bureau of); PCT/US2011/026074; 5 pages.
Heffernan et al; Temporal Cortex Synaptophysin mRNA is Reduced in Alzheimer's Disease and is Negatively Correlated with the Severity of Dementia; Experimental Neurology; 1998; 150:235-239.
Ito et al; Characterization of edema by diffusion-weighted imaging in experimental traumatic brain injury; J. Neurosurg.; 1996; 84:97-103.
Kermani et al; Brain-Derived Neurotophic Factor: A Newly Described Mediator of Angiogenesis; Trends Cardiovasc Med; 2007; 17:140-143.
Kucinski et al; Correlation of Apparent Diffusion Coefficient and Computed Tomography Density in Acute Ischemic Stroke; Stroke; 2002; 33:1786-1791.
Laske et al; Stage-dependent BDNF serum concentrations in Alzheimer's disease; J. Neural Transm.; 2006; 113:1217-1224.
Leblanc et al; Cerebral Hemorrhage from Amyloid Angiopathy and Coronary Thrombolysis; Neurosurgery; 1992; 31:586-590.
Liu et al; Hemorrhage Detection During Focused-Ultrasound Induced Blood-Brain-Barrier Opening by Using Susceptibility-Weighted Magnetic Resonance Imaging; Ultrasound in Med. & Biol.; 2008; 34(4):598-606.
Lu et al; Neurotrophins and Hippocampal Synaptic Transmission and Plasticity; Journal of Neuroscience Research; 1999; 58:76-87.
Maia et al; Clinical phenotypes of Cerebral Amyloid Angiopathy; Journal of the Neurological Sciences; 2007; 257:23-30.
Morelli et al; Insulin-degrading Enzyme in Brain Microvessels Proteolysis of Amyloid β Vasculotropic Variants and Reduced Activity in Cerebral Amyloid Angiopathy; The Journal of Biological Chemistry; 2004; 53:56004-56013.
Nagahara et al; Neuroprotective effects of brain-derived neurotrophic factor in rodent and primate models of Alzheimer's disease; Nature Medicine; 2009; 15(3):331-337.
Nicoll et al; Cerebral amyloid angiopathy plays a direct role in the pathogenesis of Alzheimer's disease Pro-CAA position statement; Neurobiology of Aging; 2004; 25:589-597.
Olichney et al; Cerebral Infarction in Alzheimer's Disease is Associated with Severe Amyloid Angiopathy and Hypertension; Arch Neurol.; 1995; 52:702-708.
Peila et al; A TGF-β1 polymorphism association with dementia and neuropathologies: The HAAS; Neurobiology of Aging; 2007; 28:1367-1373.
Pezzini et al; Cerebral Amyloid Angiopathy: A Common Cause of Cerebral Hemorrhage; Current Medicinal Chemistry; 2009; 16:2498-2513.
Premkumar et al; Apolipoprotein E-?4 Alleles in Cerebral Amyloid Angiopathy and Cerebrovascular Pathology Associated with Alzheimer's Disease; American Journal of Pathology; 1996; 148(6):2083-2095.

Prior et al; Loss of vessel wall viability in cerebral amyloid angiopathy; Neuroreport; 1996; 7:562-564.
Suzuki et al; BDNF-induced recruitment of TRKB receptor inito neuronal lipid rafts: roles in synaptic modulation; The Journal of Cell Biology; 2004; 167(6):1205-1215.
Tartaglia et al; Protein Synthesis-dependent and -independent Regulation of Hippocampal synapses by Brain-derived Neurotrophic Factor; The Journal of Biological Chemistry; 2001; 276(40):37585-37593.
Tian et al; Cerebral amyloid angiopathy and dementia; Panminerva Med; 2004; 46:253-264.
Tsenter et al; Dynamic Changes in the Recovery after Traumatic Brain Injury in Mice: Effect of Injury Severity on T2-Weighted MRI Abnormalities, and Motor and Cognitive Functions; Journal of Neurotrauma; 2008; 25:324-333.
Wang et al; The Levels of Soluble versus Insoluble Brain Aβ Distinguish Alzheimer's Disease from Normal and Pathologic Aging; Experimental Neurology; 1999; 158:328-337.
Welch et al; Automated Three-Dimensional Signature Model for Assessing Brain Injury in Emergent Stroke; Cerebrovasc Dis; 2001; 11(1):9-14.
Weller et al; Cerebral amyloid angiopathy in the aetiology and immunotherapy of Alzheimer disease; Alzheimer's Research & Therapy; 2009; 1:6-18.
Winkler et al; Spontaneous Hemorrhagic Stroke in a Mouse Model of Cerebral Amyloid Angiopathy; The Journal of Neuroscience; 2001; 21(5):1619-1627.
Wyss-Coray et al; Adult mouse astrocytes degrade amyloid-β in vitro and in situ; Nature Medicine; 2003; 9(4):453-457.
Wyss-Coray et al; Chronic Overproduction of Transforming Growth Factor-β1 by Astrocytes Promotes Alzheimer's Disease-Like Microvascular Degeneration in Transgenic Mice; American Journal of Pathology; 2000; 156(1):139-150.
Wyss-Coray et al; Increased Central Nervous System Production of Extracellular Matrix Components and Development of Hydrocephalus in Transgenic Mice Overexpressing Transforming Growth Factor-β1; American Journal of Pathology; 1995; 147(1):53-67.
Yamada et al; Risk Factors for Cerebral Amyloid Angiopathy in the Elderly; Ann. N.Y. Acad. Sci.; 2002; 977:37-44.
Zlokovic, Berislav V.; Neurovascular mechanisms of Alzheimer's neurodegeneration; Trends in Neurosciences; 2005; 28(4):202-208.
Castellani et al; Cerebral amyloid angiopathy: major contributor or decorative response to Alzheimer's disease pathogenesis; Neurobiology of Aging; 2004; 25:599-602.
Yamada et al; A Deletion Polymorphism of a2-Macroglobulin Gene and Cerebral Amyloid Angiopathy; Stroke; 1999; 30:2277-2279.
International Preliminary Report on Patentability in International Application No. PCT/US2011/026074, dated Aug. 28, 2012, 6 pages.
Sperling et al., "Amyloid Related Imaging Abnormalities (ARIA) in Amyloid Modifying Therapeutic Trials: Recommendations from the Alzheimer's Association Research Roundtable Workgroup," Alzheimers Dement. Jul. 2011 ; 7(4): 367-385.
Wilcock et al., "Aβ vaccination, but not nitro-NSAID treatment, increases vascular amyloid and microhemorrhage while both reduce parenchymal amyloid," Neuroscience. Feb. 9, 2007; 144(3): 950-96.

* cited by examiner

METHODS OF TREATING CEREBRAL AMYLOID ANGIOPATHY

CLAIM OF PRIORITY

This application is a 371 of International Application No. PCT/US2011/026074, filed Feb. 24, 2011 and claims the benefit of U.S. Provisional Application Ser. No. 61/308,678, filed on Feb. 26, 2010, all of which are incorporated herein by reference in their entireties.

FEDERALLY SPONSORED RESEARCH OR DEVELOPMENT

This invention was made with government support under Grant No. AG027437 awarded by the National Institute on Aging of the National Institutes of Health. The government has certain rights in the invention.

TECHNICAL FIELD

This invention relates to methods for treating and reducing risk of cerebral amyloid angiopathy (CAA) using mucosal, e.g., nasal, vaccination with a proteosome-based adjuvant.

BACKGROUND

Cerebrovascular dysfunction is a fundamental part of the pathology of several neurodegenerative diseases and rated as one of the most prominent cause for dementia. Cerebral amyloid angiopathy (CAA) results in intra-parenchymal and subarachnoid bleeding, which is caused by cerebrovascular amyloid deposits and multiple infarcts, and can lead to hemorrhagic stroke and cognitive impairment (Greenberg et al. Stroke. 2004; 35:2616-2619; Frangione et al. Amyloid. 2001; 8 Suppl 1:36-42). The prevalence of CAA, estimated from autopsy series, is approximately 10% to 40% of the general elderly population (Greenberg et al. Stroke. 2004; 35:2616-2619). Although the most common form of cerebrovascular amyloid is Aβ-CAA, there are other proteins that have been linked to familial forms of CAA such as: APP, cystatin C, BRI, prion protein, gelsolin, and transthyretin (Burgermeister et al. Lessons from mouse models. Ann NY Acad Sci. 2000; 903:307-316). Clinical interventions usually consist of blood pressure control (i.e., hypertension treatment) as well as avoidance of medications that increase systemic hemorrhage risk (e.g., aspirin). However, there are no current treatments to reduce amyloid pathology in CAA (Maia et al. J Neurol Sci. 2007; 257:23-30).

SUMMARY

The present invention is based, at least in part, on the discovery that nasal administration of a protosomal adjuvant has beneficial effects on clinical and pathophysiological features of CAA. Thus, the present invention includes methods of treating a subject who has CAA by nasal administration of a proteosome-based adjuvant, e.g., PROTOLLIN™.

The methods include selecting a subject who has CAA, e.g., on the basis that they have CAA, and nasally administering a therapeutically effective amount of a pro proteosome-based adjuvant as described herein. The methods can further include administering one or more clinical tests to evaluate the effectiveness of the treatment, e.g., imaging studies, e.g., MRI, angiography, positron-emission tomography (PET) or computed tomography (CT). In addition, the methods can include administering one or more treatments for CAA, e.g., surgical hematoma evacuation, or administration of a pharmaceutical such as a corticosteroid, cyclophosphamide, or other treatment for CAA.

Thus, in one aspect, the invention provides methods for treating CAA in a subject. The methods include selecting a subject who has CAA, e.g., on the basis that they have CAA; and mucosally, e.g., nasally administering a therapeutically effective amount of a proteosome-based adjuvant as described herein. In some embodiments, the methods further include diagnosing the subject with CAA, e.g., according to the Boston Cerebral Amyloid Angiopathy Group guidelines, and/or based on the presence of a single lobar, cortical, or corticosubcortical hemorrhage without another cause, multiple hemorrhages with a possible but not a definite cause, or a hemorrhage in an atypical location.

In some embodiments, the methods further include administering one or more clinical tests to evaluate the effectiveness of the treatment, e.g., imaging studies, e.g., MRI, angiography, positron-emission tomography (PET) or computed tomography (CT), or a cognitive evaluation.

In some embodiments, the methods further include administering one or more treatments for CAA, e.g., surgical hematoma evacuation, or administration of a pharmaceutical such as a corticosteroid, cyclophosphamide, or other treatment for CAA.

In another aspect, the invention provides methods for decreasing risk of recurrence of intracranial hemorrhage (ICH) in a subject who has had at least one diagnosed ICH. The methods include mucosally, e.g., nasally, administering a therapeutically effective amount of a proteosome-based adjuvant.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1: Nasal PROTOLLIN reduces brain damage in CAA mouse model. (A) Colocalization (right) of vascular amyloid (Congo red positive, left) and endothelial cells (EC) (CD31 marker, green, middle) in the brain of 16-month-old TGF-β1 Tg mice compared to age-matched non-transgenic littermates (WT). Scale bar: 10 μm. (B) T2-weighted images of TGF-β1 mice brain with and without PROTOLLIN treatment. Arrows point to lateral ventricles. (C) T2-weighted analysis of 16-month-old TGF-β1 mice (control group: PBS treated) showed significant enlargement in the lateral ventricle area (mm2) compared to 13-month-old TGF-β1 mice (***P<0.0001) and aged-matched WT mice (*P<0.001). PROTOLLIN treatment prevented further enlargement in the lateral ventricle area as compared to 13-month-old TGF-β1 mice prior to treatment and as compared to control group, 16-month-old TGF-β1 mice (**P<0.0005). Values are mean±SEM (n=6 mice per group). (D) ADC analysis is a measurement of averaged 3-dimensional diffusion of water molecules in an image pixel (mm2/sec). 16-month-old TGF-β1 mice in the control group had a significantly reduced ADC compared to WT mice (*P<0.04) and compared to the PROTOLLIN treated group (*P<0.04). Values are mean±SEM (n=5 mice per group).

FIG. 2: PROTOLLIN treatment prevents microhemorrhage incidents in CAA mouse model. (A) Brain permeability index as quantified from T1 weighted analysis showed significant increase in BBB permeability to Gadolinium DPTA in 16-month-old TGFβ1 mice as compared to the WT and PROTOLLIN treated groups (*P<0.01). Values are mean±SEM (n=5 mice per group). (B) Microhemorrhage incidents in 16-month-old TGF-β1 mice as detected by parenchymal immunostaining of fibrinogen (red, middle) in parallel to endothelial cells (CD31+, green) in comparison to WT and PROTOLLIN treated group. Scale bar: 50 µm.

FIG. 3: CAA mice treated with PROTOLLIN showed reduction in vascular amyloid. (A) Representative image of vascular amyloid deposition (Congo red, red) in brain sections of TGF-β1 Tg mice treated with PBS (control mice, upper panel) in parallel to endothelial cells (CD31+, green) in comparison to PROTOLLIN treated group (middle panel) and age-matched non transgenic littermates (lower panel). Scale bar: 100 µm. (B) Quantified analysis of the number of vessels containing amyloid deposition in brain section of 16-month-old TGF-β1 mice. Brain sections with PROTOLLIN showed a significant reduction in the number of cerebrovascular amyloid incidents compared to the control group (*P<0.03). PROTOLLIN treatment showed a higher effect in vessels with radii 20-35 µm (#P=0.05) and greater than 35 µm (*P<0.04). Values are mean±SEM (n=6-7 mice per group). (C) Aβ (1-40) levels in TGF-β1 mice treated with PROTOLLIN or PBS vs. age-matched non-transgenic littermates. Brain insoluble, soluble and plasma mouse Aβ (1-40) levels were measured by ELISA. PROTOLLIN-treated TGFβ1 mice had a significant decrease in insoluble brain Aβ (1-40) (*P<0.05), an increase in soluble Aβ (1-40) (**P<0.01), and an increase in plasma Aβ (1-40) (*P<0.05) compared to PBS treated TGF-β1 mice. Values are mean±SEM (n=6-7).

FIG. 4: PROTOLLIN treatment improved cognition in a vascular amyloid mouse model. (A) Object recognition test showed significant improvement of cognition in PROTOLLIN treated TGF-β1 Tg mice vs. control (*P<0.05, P<0.01, *P<0.006). Values are mean±SEM (n=6-7 mice per group). (B) Y-maze test showed significant (*P<0.05) improvement of cognition in PROTOLLIN-treated TGF-β1 Tg mice vs. PBS treated mice. **P<0.04. Values are mean±SEM (n=6-7 mice per group). (C) Locomotor behavior (Rotarod test) showed no significant difference between the groups, which indicates that TGF-β1 Tg mouse do not have moving dysfunction.

FIG. 5: Elevation in synatophysin following PROTOLLIN treatment. (A) Representative image of synaptophysin staining (red) in the CA3 hippocampal brain sections of TGFβ1 Tg mice. Higher reactivity observed in PROTOLLIN-treated mice vs control. Scale bar: 100 µm. (B) Quantified analysis of hippocampal synaptophysin immunoreactivity in TGF-β1 mice. Synaptophysin immunoreactive bands migrated to 38 kDa in Western blot (upper panel). In 16-month-old TGF-β1 mice there was a significant reduction (*P<0.05) in synaptophysin immunoreactivity in the hippocampus as compared to WT mice and to the PROTOLLIN-treated group (**P<0.01) (lower panel). (C) Elevation in BDNF expression in the hippocampal region of TGF-β1 mice treated with PROTOLLIN (*P<0.03) as compared to PBS treated mice. Results are presented as mean±SEM of the relative expression of the RNA compared to ACTB RNA levels.

FIG. 6: Cerebrovascular amyloid clearance in PROTOLLIN-treated mice is mediated by activated macrophages. (A) Activated perivascular macrophage cells (Iba1+, green) colocalized with a reduction of vascular amyloid deposition (Congo red, red) in the brains of PROTOLLIN-treated mice vs. the PBS-treated group (upper panel). Scale bar represents 20 µm. (B) Elevation of monocyte activation markers TNF-β (**P<0.02) and CD11b (*P<0.05) in the blood of PROTOLLIN-treated mice compared to the control group as detected by real-time PCR analysis of blood samples (n=6). Values are mean±SEM (C) Elevation of macrophage activation markers from PROTOLLIN-treated mice compared to control: SRA (P<0.02), TNFα (P<0.02), IDE (**P<0.02), CD11b (#P<0.04), CCR2 (*P<0.05), as detected in isolated macrophages. Values are mean±SEM (n=6-7).

FIG. 7: PROTOLLIN-treated macrophage clears vascular amyloid in an in situ assay. (A) Macrophage cell line (RAW264.7) was incubated on un-fixed frozen mouse brain sections with high vascular amyloid (Congo red, red) for 4 days at 37° C. with (right panel) and without (middle panel) 0.1 µg/ml PROTOLLIN. (B) Quantified analysis of cerebrovascular amyloid following incubation with macrophage using NIH image analysis. Incubation with macrophage reduced vascular amyloid (*P<0.05). PROTOLLIN activated macrophages significantly decreased amyloid deposition (P<0.0003) vs. macrophages alone as compared to control (*P<0.0001). Values are mean±SEM (n=7).

DETAILED DESCRIPTION

Described herein are methods of treating CAA using nasal administration of proteosome-based adjuvants.

Proteosome-Based Adjuvants

Proteosome-based adjuvant compositions comprise an outer membrane protein preparation of proteosomes (i.e., projuvant) prepared from Gram-negative bacteria, such as Neisseria meningitides, and optionally a preparation of one or more liposaccharides, e.g., lipopolysaccharides (LPS). The proteosome-based adjuvants can be or include lipids, glycolipids, glycoproteins, small molecules, or the like. An exemplary proteosome-based adjuvant is PROTOLLIN™, available commercially from GlaxoSmithKline, which may be prepared, for example, as described in U.S. Pat. No. 7,524,509 and U.S. Patent Application Publication Nos. 2003/0044425 and 2009/0318337. The proteosome adjuvant can be prepared with LPS (e.g., PROTOLLIN™, which comprises proteosomes non-covalently complexed with) or without LPS (see, e.g., U.S. Pat. Nos. 5,726,292 and 5,985,284, and U.S. Patent Application Publication Nos. 2001/0053368 and US 2003/0044425), and is formulated for mucosal, e.g., nasal administration.

Cerebral Amyloid Angiopathy (CAA)

CAA is caused by the deposition of amyloid protein, e.g., beta-amyloid, in the media and adventitia of small- and mid-sized arteries (and less frequently, veins) of the cerebral cortex and the leptomeninges (Pezzini et al., Curr Med Chem. 2009; 16(20):2498-513). CAA is present in some, but not all, patients with Alzheimer disease (AD), and is also often found in the brains of elderly patients who are neurologically healthy (Chung et al., J Nucl Med. December 2009; 50(12):1969-74; Weller et al., Alzheimers Res Ther. Oct. 12, 2009; 1(2):6). In one study, 400 autopsies found evidence of CAA in the brains of 18.3% of men and 28% of women aged 40-90 years. In 117 brains of patients with confirmed AD, 83% had evidence of CAA. See Ellis et al., Neurology. June 1996; 46(6):1592-6.

While CAA is often asymptomatic, it can be associated with dementia, intracranial hemorrhage (ICH), e.g., lobar ICH, or transient neurologic events. ICH is the most common clinical effect of CAA, and symptoms of an ICA are often the reason CAA is diagnosed. Symptoms include headache, coma, seizure, and nausea/vomiting. ICH can recur, often within a year of the first occurrence. Rapidly progressing dementia is also associated with CAA, as opposed to the protracted course of progressive dementia seen in AD patients. Stereotyped transient neurologic events commonly include focal weakness, paresthesias, or numbness.

The diagnosis of CAA associated with ICH can be made according to the Boston Cerebral Amyloid Angiopathy Group guidelines. Four levels of certainty in the diagnosis of CAA are considered: definite, probable with supporting pathological evidence, probable, and possible. The first 3 require that no other cause of hemorrhage has been identified.

Definite CAA: Full postmortem examination reveals lobar, cortical, or corticosubcortical hemorrhage and evidence of severe CAA.

Probable CAA with supporting pathological evidence: The clinical data and pathological tissue (evacuated hematoma or cortical biopsy specimen) demonstrate a hemorrhage with the aforementioned characteristics and some degree of vascular amyloid deposition.

Probable CAA: Clinical data and MRI findings (in the absence of a pathological specimen) demonstrate multiple hematomas (as described above) in a patient older than 60 years.

Possible CAA: This is considered if the patient is older than 60 years, and clinical and MRI data reveal a single lobar, cortical, or corticosubcortical hemorrhage without another cause, multiple hemorrhages with a possible but not a definite cause, or some hemorrhage in an atypical location Imaging studies, such as MRI, angiography, Positron-emission tomography (PET) or computed tomography (CT) scanning, can be used to assist in the diagnosis of CAA.

The present methods can be used in combination with other treatments for patients with CAA, such as reversing anticoagulation, managing intracranial pressure, and preventing complications; the co-administration of steroids (e.g., corticosteroids) and/or cyclophosphamide can also be used. Where appropriate, surgical evacuation of hematoma can also be performed to lower intracranial pressure, e.g., when a hematoma causes significant mass effect and predisposes to herniation, and/or when medical management of increased intracranial pressure is ineffective.

Subjects who are at risk of developing CAA can include those with a family history of CAA, or a genetic predisposition to CAA, e.g., a mutation in apolipoprotein E (APOE), presenilin 1 (P51), α1-antichymotrypsin (ACT), butyrylcholinesterase, α2-macroglobulin, and/or paraoxonase (see, e.g., Premkumar et al., Am J Pathol. 1996 June; 148(6): 2083-95; Yamada, Ann NY Acad Sci. 2002 November; 977:37-44; Yamada et al., Stroke. 1999 November; 30(11): 2277-9).

For additional information regarding CAA, see Menon et al., "Cerebral Amyloid Angiopathy," available at emedicine.medscape.com/article/1162720-print.

CAA and Alzheimer's Disease (AD)

In AD, the β-amyloid (Aβ) (1-40) peptide forms amyloid plaques in the cerebrovasculature and it is associated with endothelial cell (EC) thinning and loss of endothelial mitochondria, which leads to blood-brain barrier (BBB) dysfunction (Nicoll et al. Neurobiol Aging. 2004; 25:589-597; discussion 603-584; Castellani et al. Neurobiol Aging. 2004; 25:599-602; discussion 603-594; Farfara et al. J Cell Mol Med. 2008; 12:762-780). AD is associated with the neuronal dysfunction induced by senile plaque (SP) formation and neurofibrillary degeneration. CAA and AD have distinct pathologies and are distinct disease entities, with non-coextensive patient populations. Although the Abeta protein deposited within blood vessels in CAA is similar in chemical composition to that deposited in the brain parenchyma in SP, there is no clear relationship between the two pathologies. Indeed, when CAA is high, SP formation may be low, and vice versa. As if to emphasise these differences, Abeta within CAA is mostly Abeta40 whereas that within SP is Abeta42. Such compositional differences may reflect differences in source, with Abeta in SP being derived from nerve cells and Abeta in CAA having a local vascular origin (Tian et al., Panminerva Med. 2004 December; 46(4):253-64). It was reported that CAA is detected in 80% of patients diagnosed with Alzheimer's disease (AD) (Nicoll et al. Neurobiol Aging. 2004; 25:589-597; discussion 603-584; Castellani et al. Neurobiol Aging. 2004; 25:599-602; discussion 603-594; Zlokovic. Trends Neurosci. 2005; 28:202-208); not every patient who has AD has or will get CAA, and not every patient with CAA has or will get AD.

Impaired clearance of Aβ from the brain is thought to be one of the main causes of amyloid accumulation in sporadic AD. Several endogenous mechanisms exist for the removal of soluble Aβ from the central nervous system (CNS) to the periphery, including receptor-mediated clearance at the BBB and via perivascular macrophages, that in light of their localization within perivascular spaces and proximity to vascular amyloid. It was previously suggested to play a role in regulating the deposition of vascular Aβ (see Hawkes and McLaurin PNAS USA 106(4):1261-1266 (2009)

Transforming Growth Factor-β1 Transgenic Mouse Model of CAA

Transforming growth factor-β1 (TGF-β1) is a multifunctional cytokine that is a major regulator of the immune response; it has profound effects on vasculogenesis, angiogenesis, and the maintenance of vessel wall integrity. Furthermore, cortical TGF-β1 messenger RNA (mRNA) levels correlate positively with the degree of cerebrovascular amyloid deposition in AD cases, and TGF-β1 immunoreactivity in such cases is elevated along the cerebral blood vessels (Wyss-Coray et al. Am J Pathol. 2000; 156:139-150). Positive correlation was found between transforming growth factor-β1 (TGF-β1) polymorphisms and CAA (Peila et al. Neurobiol Aging. 2007; 28:1367-1373).

Transgenic overexpression of TGF-β1 under the control of an astrocyte glial fibrillary acidic protein (GFAP) promoter in mice, causes an age-related (starting at the age of 8 months) deposition of amyloid around cerebral blood vessels and prominent perivascular astrocytosis (Wyss-Coray et al. Am J Pathol. 1995; 147:53-67), leading to CAA-related vascular alterations and dysfunction.

Methods of Treatment

The methods described herein include methods for the treatment of CAA. In some embodiments, the CAA is associated with ICH. Generally, the methods include mucosally, e.g., nasally, administering a therapeutically effective amount of a proteosome-based adjuvant as described herein, to a subject who is in need of, or who has been determined to be in need of, such treatment. Mucosal administration can be performed as known in the art, e.g., by inhalation, or absorption, e.g., via nasal, intranasal, pulmonary, buccal, sublingual, rectal, or vaginal administration.

As used in this context, to "treat" means to ameliorate at least one symptom of the disorder associated with CAA. Often, CAA results in an increased risk of ICH, dementia, or transient neurologic events; thus, a treatment can result in a reduction in risk of ICH, dementia, or transient neurologic events, and/or a return or approach to normal cognitive function. Administration of a therapeutically effective amount of a compound described herein for the treatment of CAA will result in decreased levels and/or decreased rate of amyloid deposition in the cerbrovasculature.

For the purpose of mucosal therapeutic administration, the proteosome-based adjuvant is in a form suitable for administration by inhalation or absorption, e.g., via nasal sprays or drops, or rectal or vaginal suppositories. In some embodiments the adjuvant is optionally incorporated with excipients or carriers. In some embodiments, for administration by inhalation, the proteosome-based adjuvant can be delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal means. In some embodiments, for transmucosal administration, penetrants appropriate to the barrier to be permeated can be used in the formulation. Such penetrants are generally known in the art, and include, for example, for transmucosal administration, detergents, bile salts, and fusidic acid derivatives. Transmucosal administration can be accomplished through the use of nasal drops or sprays, or rectal or vaginal suppositories.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. In some embodiments, a dosage range is about 1 ug-100 ug per dose.

EXAMPLES

The invention is further described in the following examples, which do not limit the scope of the invention described in the claims.

Example 1

Nasal vaccination with a proteosome-based adjuvant (PROTOLLIN), comprising of purified outer membrane proteins of Neisseria meningitides and lipopolysaccharide, which is well tolerated in humans, decreased parenchymal Aβ deposition in an AD mouse model (Frenkel et al. Ann Neurol. 2008; 63:591-601). The experiments described herein included monitoring CAA progression by non-invasive magnetic resonance imaging (MRI) in TGF-β1 mice. As demonstrated herein, nasal vaccination with PROTOLLIN decreases vascular amyloid, reduces brain damage and improves functional outcome in an animal model of CAA.

Materials and Methods

Mice.

Heterozygous TGF-β1 mice were received from Tony Wyss-Coray laboratory (Wyss-Coray et al. Am J Pathol. 1995; 147:53-67) and maintained on an inbred with a C57BL/6J genetic background (The Jackson Laboratory, Bar Harbor, Me.). All animal care and experimental use was in accordance with the Tel Aviv University guidelines and approved by the TAU animal care committee.

Cell Culture.

Murine macrophage-like RAW264.7 cells were cultured as previously described (Fujimori et al. Eur J Pharmacol. 2001; 415:95-103) and maintained at 37° C., 5% $CO_2$ and 95% relative humidity.

Nasal Vaccination.

PROTOLLIN was obtained from GlaxoSmithKline (Laval, Quebec, Canada). PROTOLLIN (28.6 μg/kg) was given nasally on days 1, 3, and 5 of the first week followed by a weekly boost (Frenkel et al. Ann Neurol. 2008; 63:591-601). Mice received a weekly boost beginning at age 13 months until age 16 months. Phosphate-buffered saline (PBS) was used as a control.

Behavioral Tests

Object Recognition Test.

Following 3 months of treatment with PROTOLLIN or PBS, the mice were tested using a novel object recognition test (ORT). Object recognition is distinguished by more time spent interacting with the novel object (Bevins et al. Nat Protoc. 2006; 1:1306-1311). Memory was operationally defined by the discrimination index for the novel object (DI) as the proportion of time the mice spent investigating the novel object and the familiar one.

Y-Maze Test.

Behavioral testing was conducted in a Plexiglas Y-maze. In brief, the first trial (training) lasted 5 min and allowed the mouse to explore only two arms (Start and Other) of the maze, with access to the third arm (Novel) blocked off. After 2 min ITI, the second trial (retention) was conducted, during which all three arms were accessible; the mouse was returned to the same 'Start' arm and allowed to explore all three arms for 2 min. Data is expressed as total time spent in the 'Novel' arm during the 2 min retention period (Akwa et al. Proc Natl Acad Sci USA. 2001; 98:14033-14037).

Rotarod Test.

Motor coordination and balance were tested with the Rotarod test as previously described (Fowler et al. Int. J. Dev. Neurosci. 20, 309-321 (2002)). The Rotarod test was performed by placing a mouse on a rotating drum (ENV-576M, Med Associate Inc, Georgia, Vt.) for 5 min habituation, 2 min rest and a test session of no longer than 2 min. The time the animal succeeded in maintaining balance on the rod during the test session was measured.

Magnetic Resonance Imaging.

TGF-β1 mice (treated with PROTOLLIN or PBS) and age-matched wt littermates (treated with PBS) were analyzed by MRI (5-7 animals in each group) as previously described (Tsenter et al. J Neurotrauma. 2008; 25:324-333). In brief, mice were anesthetized with isoflurane (1-3%) in 1 liter/min oxygen 98% and were scanned in a 7T/30 spectrometer (Bruker, Rheinstetten, Germany) using a 10 mm quadrature surface coil dedicated to mice heads and 400 mT/m gradient system. The MRI protocol included multi-echo T2weighted images (RARE, TR/TE 3000/50 ms, RARE factor 8, 4 averages), diffusion-weighted echo planar images (DWI-EPI, TR/TE=3000/25 ms, 4 EPI segments, $\Delta/\delta=10/4.5$ ms, b-value 1000 s/mm$^2$ acquired at 16 noncollinear gradient directions) and contrast enhanced T1 weighted images (SE, TR/TE 600/12 ms, 2 averages) acquired before and 3 and 5 min post ip injection (0.5 mmol/kg Gadopentetate Dimeglumine-Gadolinium DPTA) 150 μl, Magnetol, Soreq, Israel) through an ip catheter. In all experiments the field of view (FOV) was 20×20 mm$^2$, 12 axial contiguous slices of 1 mm thickness, matrix dimensions of 256×128 (zero filled to 256×256) and 128×96 (zero filled to 128×128) for the DWI-EPI experiment. Analysis was performed with the Medical Image Analysis (MIA, version 2,4 MATLAB).

Amyloid Quantification.

The right hemisphere of each mouse in each treatment group was homogenized with PBS containing protease inhibitor and centrifugated at 40,000 g for 40 min to quantify Aβ levels. The supernatant-containing soluble Aβ was stored at −70° C. The pellet containing insoluble Aβ was extracted in 5.0M guanidinium-chloride (pH 8) for 3 h at room temperature. Levels of Aβ (1-40) in brain samples and plasma, were assessed by enzyme-linked immunosorbent assay (ELISA) as previously described (DeMattos et al. Science. 2002; 295:2264-2267).

Immunohistology.

Mice were sacrificed (transcardially punctured, and saline-perfused) and their brains rapidly excised and frozen. The brains (left hemisphere) were cut in 14 μm coronal sections at −20° C. and used for histological examination. Brain sections (1.44 mm lateral to bregma) were stained with Congo red (Sigma-Aldrich) and visualized by fluorescence microscopy for quantification of the amount of vascular amyloid depositions. For immunostaining the following antibodies were used: microglia/macrophages iba1 (1:1000) [016-20001; Wako], CD31 (1:75), GFAP (1:250) [(G9269; Sigma-Aldrich], fibrinogen (1:400; DakoCytomation), synaptophysin (Epitomics, 1:250). Quantification was done for 2 consecutive sections (14 μm) per animal, with 4-6 animals per group examined. The quantification was done in a blinded fashion using Nikon NIS imaging software analysis Real-Time PCR Analysis.

Total RNA was extracted from the right hippocampus, blood samples or peripherial macrophages, was analyzed for messenger RNA expression via reverse transcription followed by real-time polymerase chain reaction (PCR) using TaqMan. Reverse transcriptase PCR assays were designed by Applied Biosystems (Foster City, Calif.) as described previously (Zhang et al. Mol Vis. 2005; 11:887-895).

Western Blotting.

For protein analysis the hippocampus was dissected out from TGF-β1 mice and homogenized in lysis buffer as previously described (Mitchell et al. Arch Biochem Biophys. 2007; 467:185-192). Proteins were transferred onto nitrocellulose membrane and probed with a polyclonal antisynaptophysin antibody (Epitomics, 1:25,000) overnight. After incubation with the primary antibody, membrane was incubated for 1 h with goat a rabbit (1:10,000, LICOR) antibody. Blots were then scanned using the Odyssey Imaging System from LICOR and normalized to tubulin (1:25,000, Sigma-Eldrich). Relative band intensity was determined using Odyssey software version 1.0 (LI-COR).

In Situ Vascular Amyloid Clearance.

10 μm sagital brain sections were prepared from 16-month-old transgenic mice using cryostat. 6×10$^5$ RAW 264 cells were exposed to 0.1 μg/ml PROTOLLIN and another set of 6>10$^5$ RAW 264 cells were left untreated. In either case, these cells were plated to unfixed brain sections enriched with vascular amyloid and incubated at 37° C. for 4 days. Brain sections were then stained with Congo red (Sigma-Aldrich). Quantification of vascular amyloid depositions was done as previously described (Frenkel et al. J Clin Invest. 2005; 115:2423-2433). The staining was performed on 6 consecutive sections per animal and repeated 4 times.

Statistical Analysis.

Data comparisons were performed using the Student's t test when two groups were compared, or one-way ANOVA analysis of variance when three or more groups were analyzed. A P value of <0.05 was considered significant.

Cerebrovascular Amyloid Deposition Results in Brain Tissue Damage in TGF-β1 Animal Model.

Figure 1A:
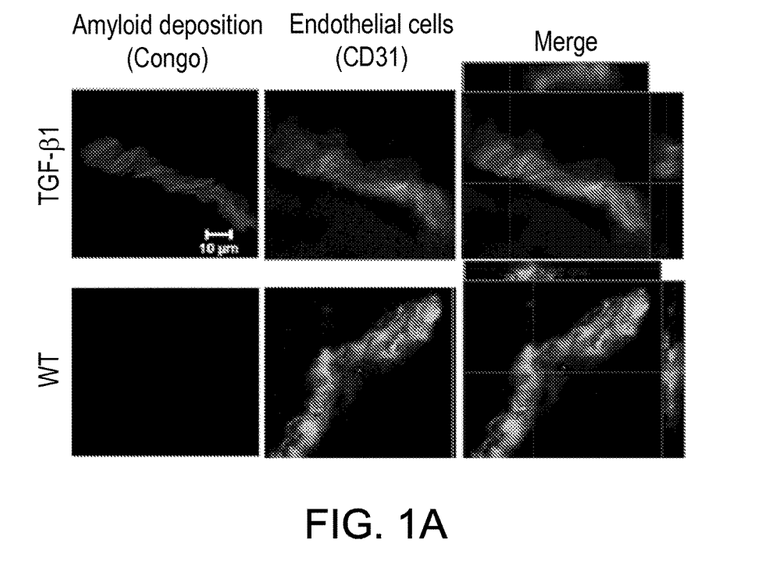
Figure 1B:
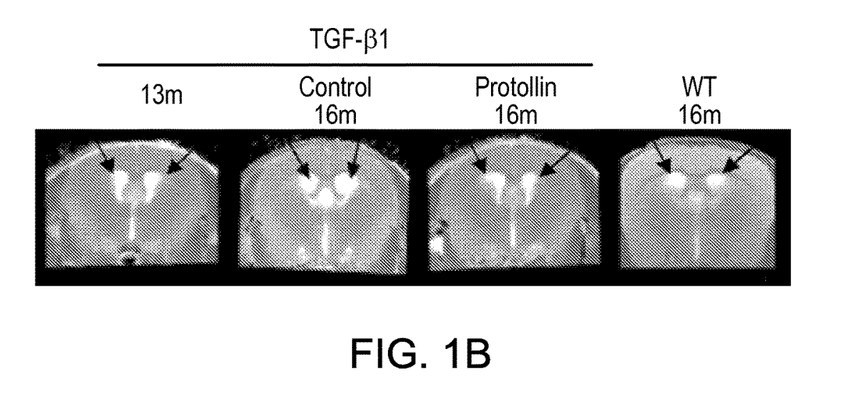
Figure 1C:
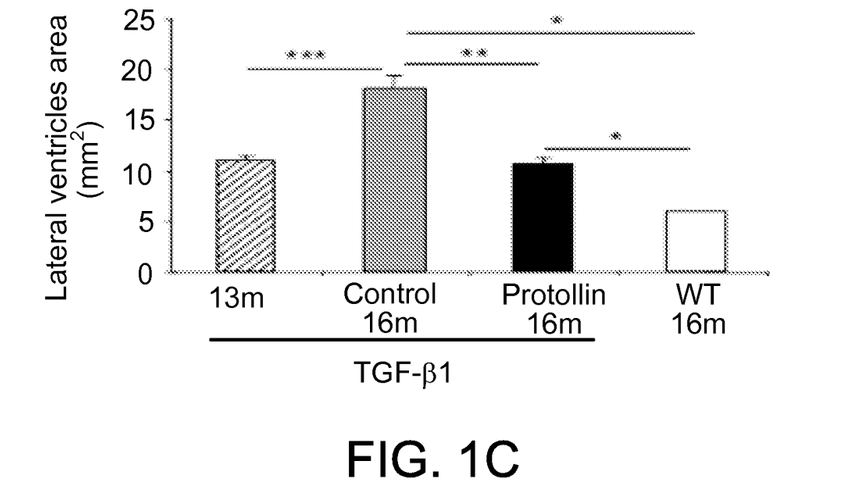
Figure 1D:
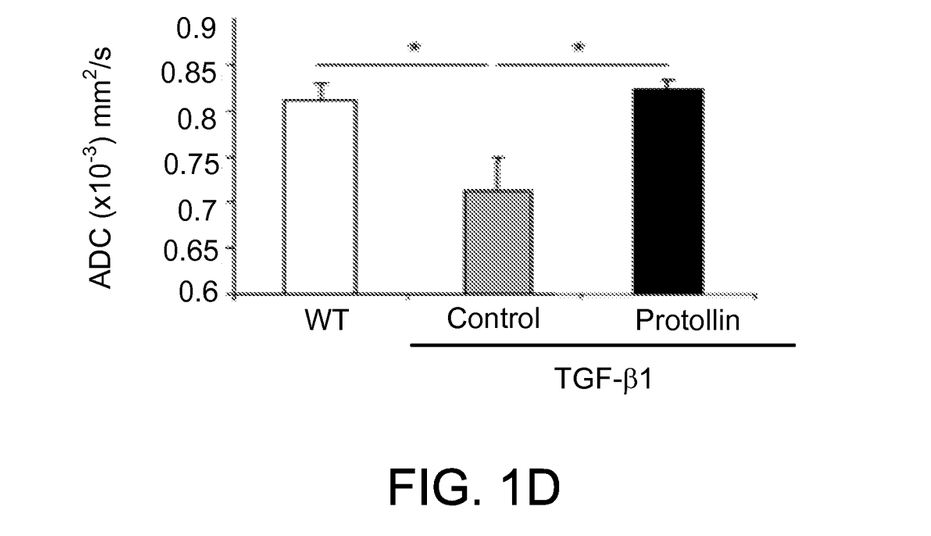

Microscopic examination of brains from 16-month-old TGF-β1 Tg mice showed significant amyloid accumulation around cerebral blood vessels, as determined by Congo red staining (FIG. 1A) and colocalization with endothelial cells (CD31 marker), compared to age-matched non-transgenic wild-type (WT) littermates. To investigate the influence of PROTOLLIN on the course of CAA in mice, 13-month-old TGF-β1 Tg mice and age-matched non-transgenic littermates mice (WT mice) were nasally administered with PROTOLLIN or PBS weekly for 3 months. Disease progression was monitored by non-invasive magnetic resonance imaging (MRI). We used two different MRI protocols: 1) T2 weighted images to assess brain tissue damage as measured by enlargement of the lateral ventricle area; 2) Apparent diffusion coefficient (ADC) which is a measurement of the diffusion of water molecules in tissue and may predict tissue damage. Using T2 weighted analysis (FIGS. 1B, C), we found that in 16-month-old TGF-β1 mice there is a 200% (P<0.001) enlargement of the lateral ventricles area as compared with age matched non-transgenic littermates and 70% (P<0.0001) compared to 13-month-old TGF-β1 mice. Nasal treatment with PROTOLLIN for 3 months (starting at the age of 13 months) prevented further enlargement of the lateral ventricles (FIGS. 1B, C). ADC has previously been shown to be reduced following stroke (Welch et al. Cerebrovasc Dis. 2001; 11 Suppl 1:9-14). Furthermore, we found, (FIG. 1D) that while in the control group there is a significant reduction in ADC at the age of 16 months, PROTOLLIN treatment prevents further damage.

Nasal Vaccination with Protosome Based Adjuvant Reduces Cerebrovascular Amyloid and Prevents Microhemorrhage.

Figure 2A:
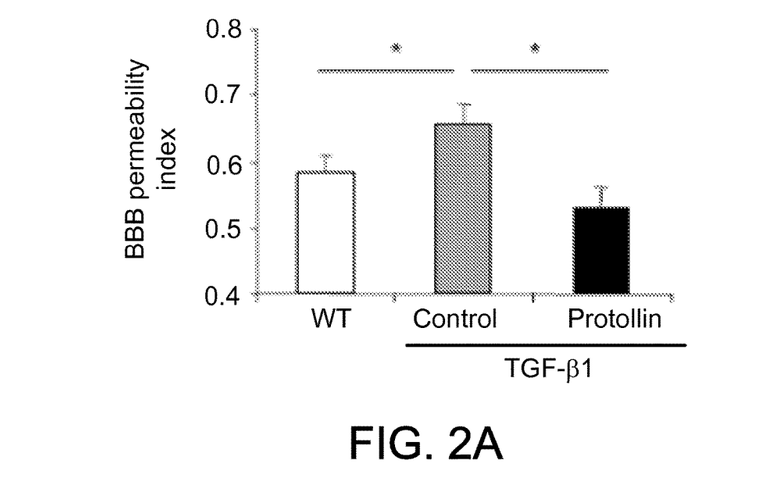

The severity of CAA has been associated with increased microhemorrhaging in human studies and animal models of AD (Hawkes et al. Proc Natl Acad Sci USA. 2009; 106: 1261-1266). Contrast enhanced (CE) T1 weighted images, measuring gadolinium (Gd-DTPA) penetration through the blood-brain barrier (BBB), were used for microhemorrhage detection (to detect the increase in the BBB permeability). We observed a 12% (P<0.01) increase in BBB permeability in 16-month-old TGF-β1 mice compared to WT (FIG. 2A), as revealed by higher intensity signal. After PROTOLLIN treatment, the BBB permeability index (signal intensities on T1-weighted MRI) was the same in Tg and wt mice.

Figure 2B:
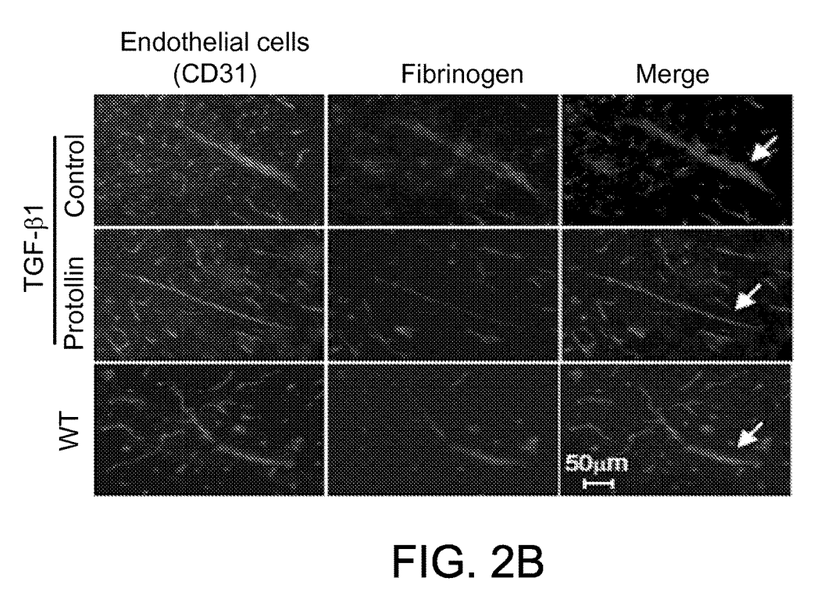

To further assess our results, we used an immunohistological approach to investigate BBB pathology leading to a penetration of the plasma protein, fibrinogen, to the parenchyma (FIG. 2B). Brain tissues from 16-month-old TGF-β1 mice demonstrated diffuse regions of parenchymal fibrinogen staining external to blood vessels (upper right panel). In the PROTOLLIN treated group, fibrinogen showed considerable areas of overlap with endothelial cells indicating well-defined blood vessels similar to those found in WT mice (middle right and lower right panels, respectively). The histology findings confirm the evidence of brain tissue microhemorrhage in Tg mice. These results, point to a generalized pattern of vascular abnormalities (leakiness of BBB to endogenous blood proteins) in TGF-β1 mice tissue and suggests that PROTOLLIN treatment can reduce pathological changes in the BBB.

Figure 3A:
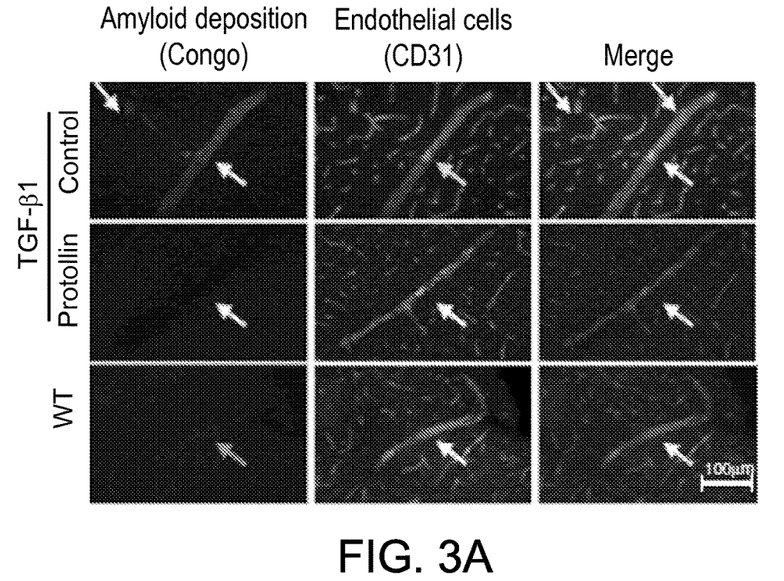
Figure 3B:
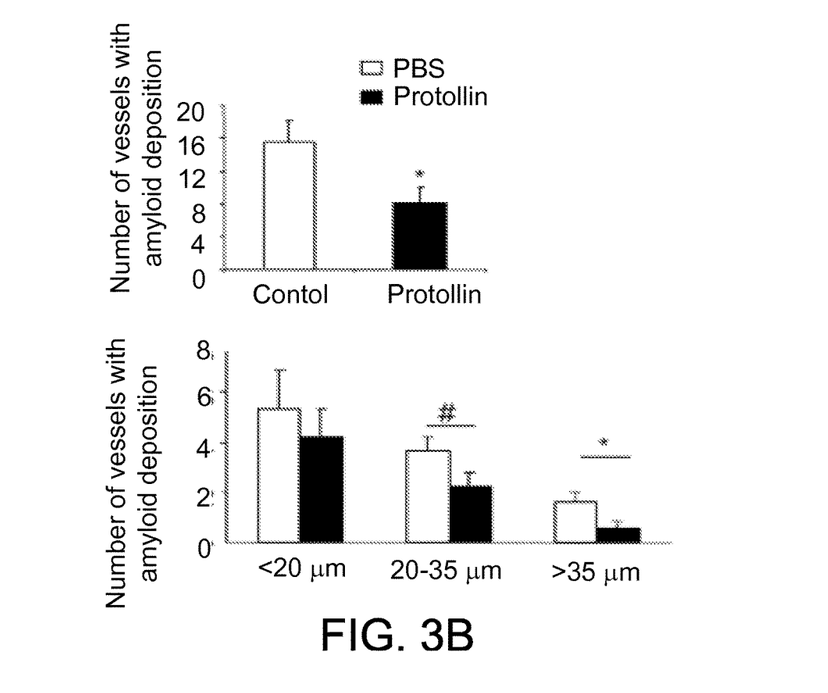

We found that vascular amyloid deposition was prominent in the leptomeninges vessels and parenchyma vessels of 16-month-old TGF-β1 mice compared to WT mice, as revealed by Congo red staining (FIG. 3A). PROTOLLIN treatment significantly (P<0.03) reduced by 48% the incidence of cerebrovascular amyloid (FIG. 3B, upper panel). PROTOLLIN treatment showed a higher effect in vessels with radii 20-35 µm (P=0.05) and greater than 35 µm (P<0.04). (FIG. 3B, lower panel).

Nasal PROTOLLIN Reduces Brain Aβ (1-40) Levels.

Figure 3C:
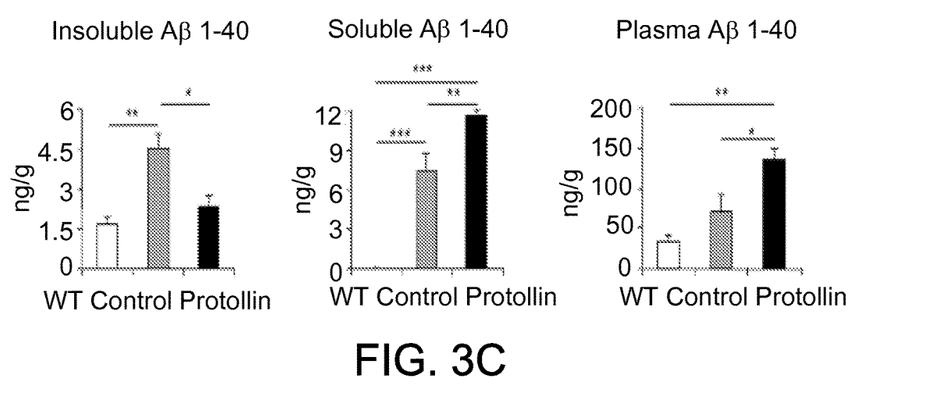

It was shown that large parts of the amyloid in the TGF-β1 mice is extracellular matrix and it was speculated that basement membrane proteins will also trap endogenous proteins such as Aβ (1-40) leading to CAA (Wyss-Coray et al. Am J Pathol. 2000; 156:139-150). We further investigated the levels of endogenous Aβ (1-40), as an indication of cerebrovascular amyloid, by ELISA (Frenkel et al. J Clin Invest. 2005; 115:2423-2433). Brains of 16-month-old TGF-β1 mice (FIG. 3C) showed a significant increase in levels of both soluble and insoluble mouse endogenous Aβ (1-40) compared to WT. Nasal PROTOLLIN significantly (P<0.05), reduced the insoluble fraction (2.34±0.4 vs. 4.5±0.6 ng/gr) and increased the soluble fraction (11.7±0.4 vs. 7.4±1.38 ng/gr) of Aβ (1-40) in the brain and plasma (135±15.4 vs. 72±20 pg/ml) (P<0.01 and P<0.05, respectively). Our data suggests that PROTOLLIN treatment leads to a progressive shift of insoluble brain Aβ (140) to soluble, reducing CAA and demonstrating the important role of a peripheral mechanism for amyloid clearance.

Nasal PROTOLLIN Improves Cognition in an Animal Model.

Figure 4A:
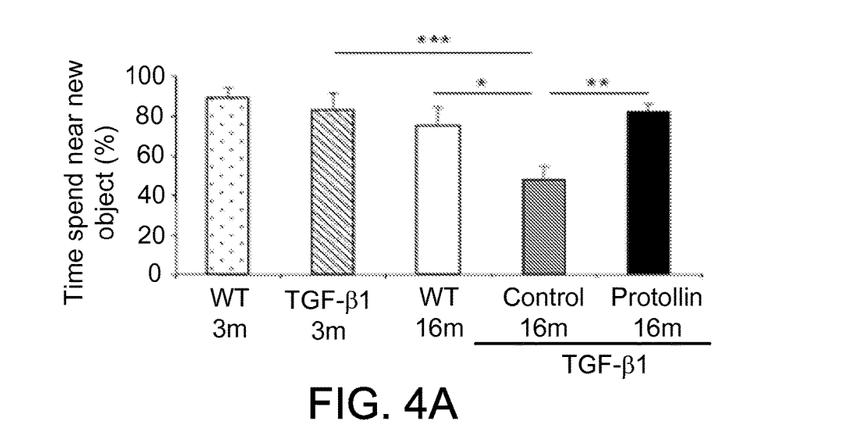
Figure 4B:
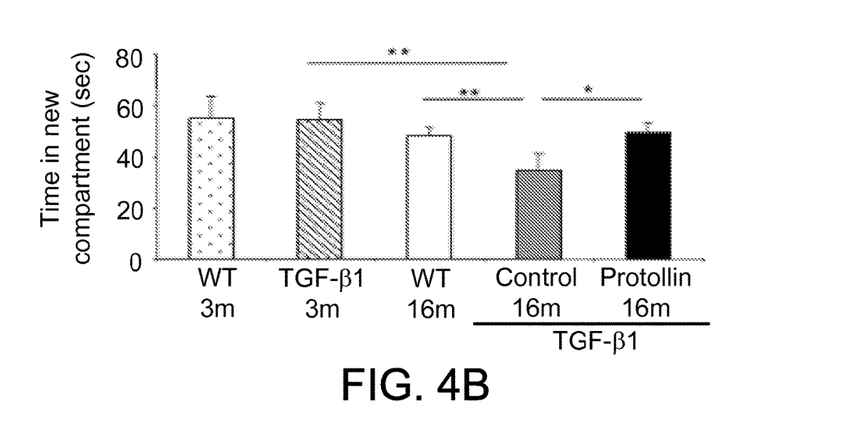
Figure 4C:
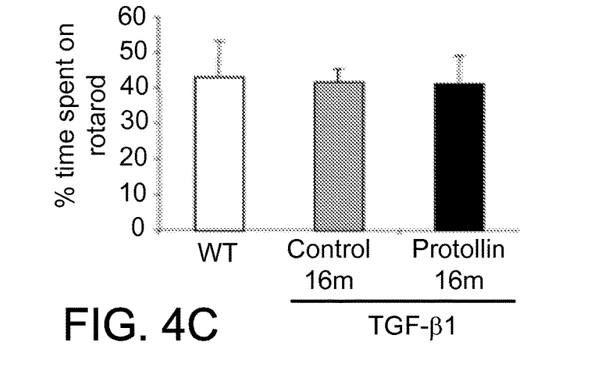

Vascular dementia (VaD) is the second most common cause of dementia in the elderly, after Alzheimer's disease (AD) and described as a multifaceted cognitive decline resulting from cerebrovascular injury to brain regions associated with memory (Lifshitz et al. Animal Models for Cerebrovascular Impairment and its Relevance in Vascular Dementia. in Cognitive Impairment: Causes, Diagnosis and Treatments. 2009; Editor: Melanie L. Landow). We investigated the cognition of aged TGF-β1 mice to determine whether CAA in those mice can lead to cognitive impairment and whether PROTOLLIN treatment can ameliorate memory dysfunction. To evaluate cognitive function, two behavioral tests were used: 1) object recognition test (ORT) to investigate visual recognition memory; 2) Y-maze test to investigate spatial perception. We found that 3-month-old mice, prior to signs of CAA (data not shown), show no observable difference in cognition between TGF-β1 Tg mice and age matched littermates. However, at 16 months old, after CAA is well established (FIG. 1A), there is significant cognitive impairment in TGF-β1 Tg as measured both by the ORT and Y-maze tests (P<0.05 and P<0.04, respectively) (FIGS. 4A,B). Furthermore, amelioration of CAA following PROTOLLIN treatment (FIG. 3A) improved memory in TGF-β1 Tg mice (FIGS. 4A, B). In order to assess that the impairment of TGF-β1 mice in ORT and Y-maze test were linked to their cognitive impairment and not motor dysfunction, we used a Rotarod test. No motor disabilities were observed in TGF-β1 Tg mice as compared to the WT or PROTOLLIN treated groups (FIG. 4C).

Nasal PROTOLLIN Increases Hippocampal Expression of Marker Proteins for Synaptic Plasticity.

Figure 5A:
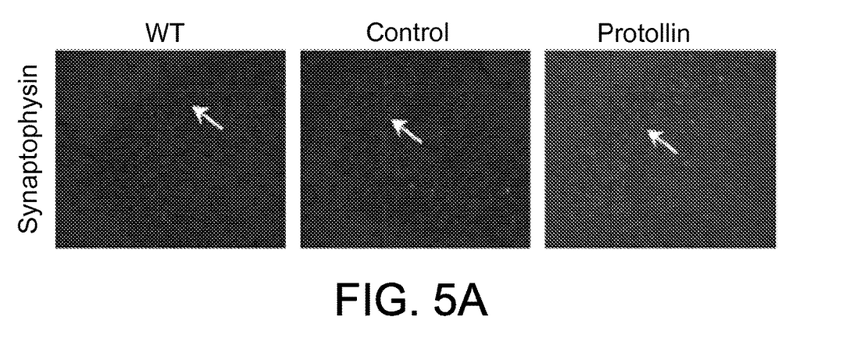
Figure 5B:
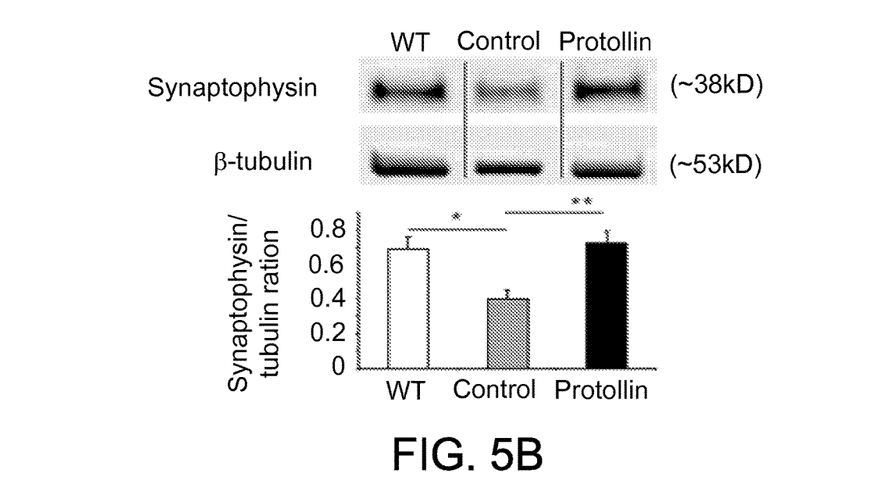
Figure 5C:
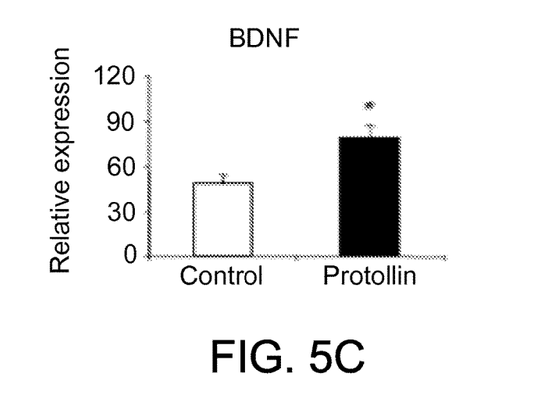

Previous work showed a reduction in synaptophysin immunoreactivity as a marker for synaptic loss in the hippocampus, and in correlation to cognitive decline in an animal model (Buttini et al. J Neurosci. 2005; 25:9096-9101). Our findings showed a reduction in synaptophysin in the hippocampus (in CA3 region) of 16-month-old TGF-β1 Tg mice compared to WT mice both by immunohistology (FIG. 5A) and Western blot (by 40%) (P<0.05) (FIG. 5B). PROTOLLIN treatment results in 45% (P<0.01) increase in synaptophysin expression levels in TGF-β1 mice (FIG. 5B, lower panel). Reports suggest a reduction in brain-derived neurotrophic factor (BDNF) protein in the hippocampus in Alzheimer's disease (Connor et al. Brain Res Mol Brain Res. 1997; 49:71-81) and that administration of BDNF may further prevent cell death and ameliorate behavioral deficits in several animal models of AD (Nagahara et al. Nat Med. 2009; 15:331-337). Furthermore, it was reported that BDNF has an important role in angiogenesis (Kermani et al. Trends Cardiovasc Med. 2007; 17:140-143). We found that BDNF was significantly increased (by 60%, P<0.03) in the hippocampus region of PROTOLLIN treated mice vs. control group (FIG. 5C). BDNF, which is known to modulate the levels of the vesicle proteins such as synaptophysin at the hippocampus synapses, was positively correlated with synaptophysin values.

Nasal PROTOLLIN Activates Macrophage to Clear Cerebrovascular Amyloid Deposition.

Figure 6A:
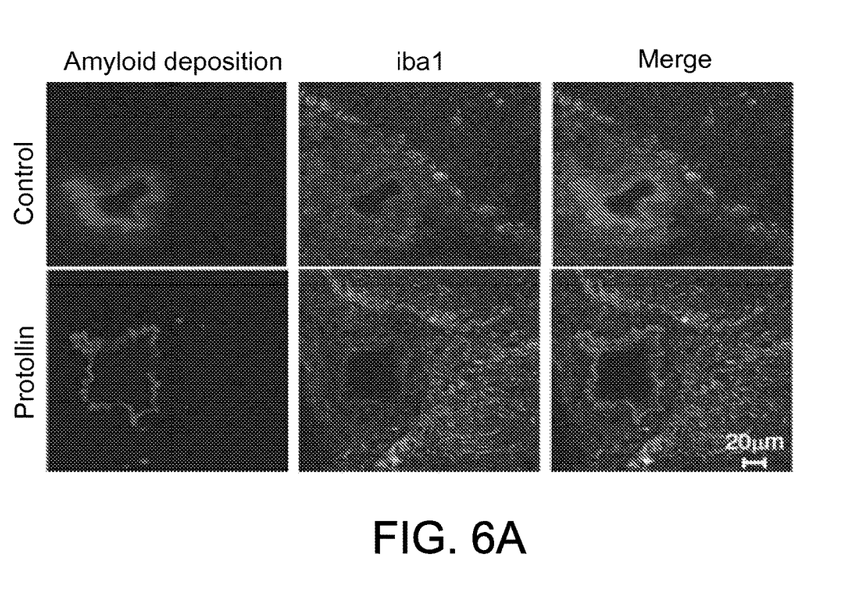
Figure 6B:
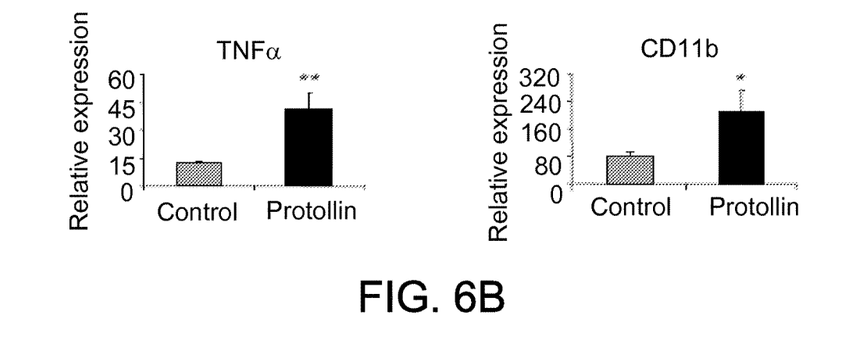
Figure 6C:
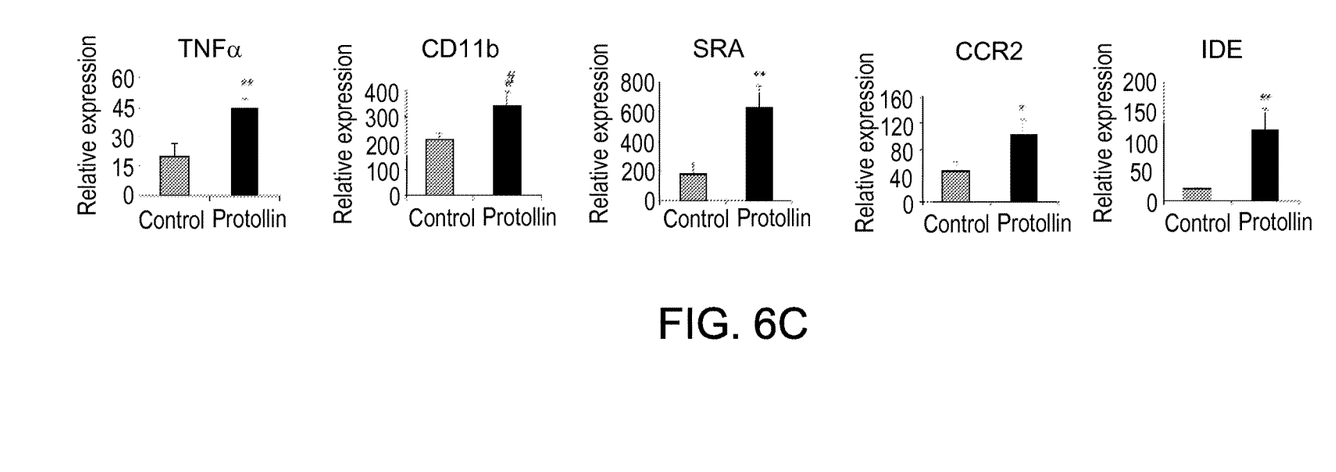

It was suggested that vascular amyloid deposits may result from impaired clearance of Aβ (1-40) by macrophages along perivascular spaces (Hawkes et al. Proc Natl Acad Sci USA. 2009; 106:1261-1266). In addition, other matrix proteins are likely to be cleared by macrophages. We observed elevation of perivascular macrophages in PROTOLLIN treated mice (FIG. 6A), which is linked to a reduction in cerebrovascular amyloid. Furthermore, we found significantly increased expression of monocyte activation markers, such as TNFα (by 227%, P<0.02) and CD11b (by 158%, P<0.05), in the blood of PROTOLLIN treated mice, by Real-Time PCR analysis (FIG. 6B). Analysis of isolated macrophages from PROTOLLIN treated mice as compared to the control group showed a significant increase (FIG. 6C) in the levels of macrophage activation markers: a 58% (P<0.04) increase in the expression of CD11b, and an 122% (P<0.02) increase in the TNF-α expression. Furthermore we found a significant increase in macrophage markers that were previously described to be important for amyloid clearance (Farfara et al. J Cell Mol Med. 2008; 12:762-780): —a 266% (P<0.02) increase in scavenger receptor A (SRA) expression, a 498% (P<0.02) increase in insulin-degrading enzyme (IDE) involved in Aβ degradation and an 120% (P<0.05) increase in chemokine receptor CCR2 which was recently linked to macrophage migration toward amyloid deposits (El Khoury et al., Nat. Med 13:432-438 (2007)).

PROTOLLIN Activates Macrophage to Degrade Vascular Amyloid In Situ.

Figure 7A:
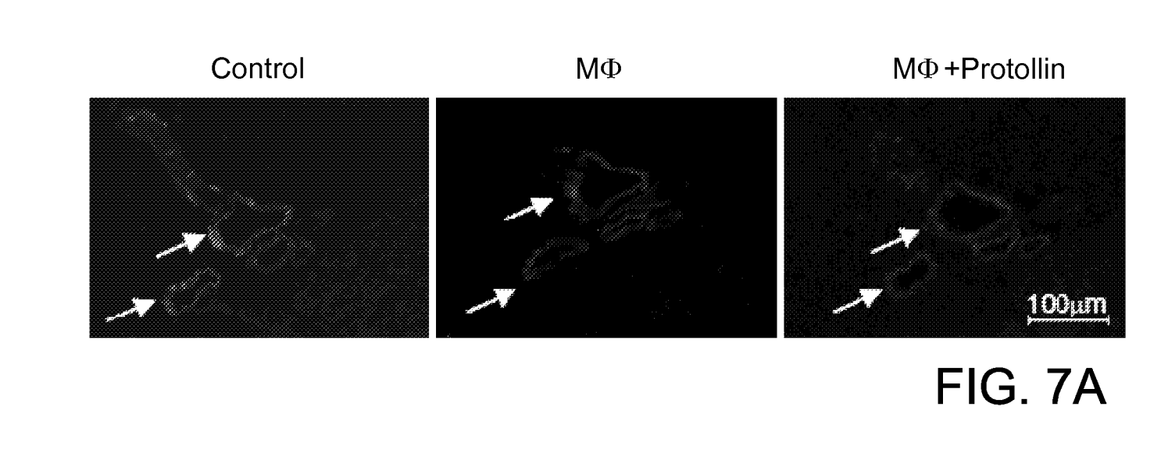
Figure 7B:
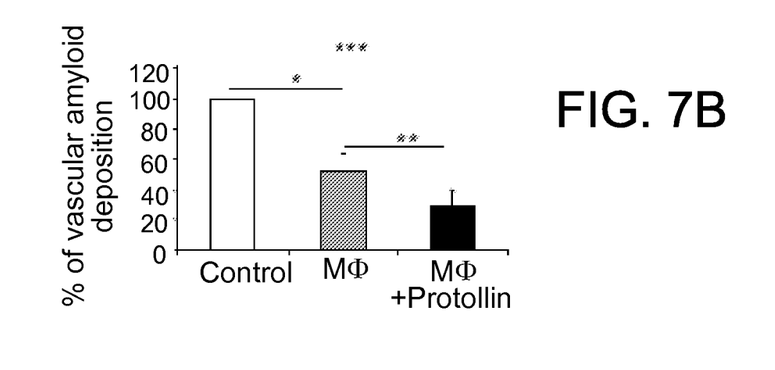

To directly determine the effect of PROTOLLIN on phagocytosis of vascular amyloid deposition by macrophages, we established an in situ assay as previously described (Wyss-Coray et al. Nat Med. 2003; 9:453-457). In brief (FIG. 7), macrophage (RAW 264.7 macrophage cell line) were plated on unfixed insoluble CAA rich brain sections from transgenic mice with or without 0.1 μg/ml PROTOLLIN for 4 days (FIG. 7A). We found that PROTOLLIN-activated macrophages significantly decreased amyloid deposition by 71% (P<0.0001) compared to control (only medium), and 43% (P<0.0003) as compared to macrophage alone (FIG. 7B).

Discussion

In the present study, we investigated a novel immunotherapeutic approach for the reduction of amyloid depositions in a mouse model of CAA. This study demonstrates that chronic elevation of TGF-β1 production of astrocytes in 16-month-old transgenic mice leads to pathological signs: vascular and meningeal amyloid deposition, brain tissues damage and cognitive impairment. Treated animals exhibited no changes in behavior, as measured by body weight, eating habits, tail tone, or mobility, that would indicate toxicity.

Patients with CAA also have a higher risk of developing hemorrhages and ischemic stroke (Olichney et al. Arch Neurol. 1995; 52:702-708). We aimed to monitor vascular disease progression in a CAA animal model using MRI approach as done in humans, to allow translation of this approach to clinical use. BBB permeability increases with advancing age, in patients with Alzheimer's disease and vascular dementia (Farrall et al. Neurobiol Aging. 2007). The focal increase in the signal intensity change on the contrast-enhanced T1-weighted images, caused by leakage of the contrast agent (Gd-DTPA) into the surrounding tissue, was used in this study to detect the increase of BBB permeability (Liu et al. Ultrasound Med Biol. 2008; 34:598-606). In TGF-β1 mice, there is a significant increase in the passage of Gd-DTPA across the BBB, compared to wt mice. PROTOLLIN treatment prevented pathological BBB permeability in TGF-β1 mice to similar levels as in wt mice and was in correlation with a reduction of microhemorrhage as detected by immunostaining Blood vessel diseases, affecting mainly the elderly population, often result in typical T2 MRI findings that include region-specific volume loss, enlargement of the lateral ventricles, and patchy areas of abnormal signal intensity within the white matter and basal ganglia (Tsenter et al. J Neurotrauma. 2008; 25:324-333). We found in conventional T2 MRI (FIG. 2A) that control mice had significant enlargement of lateral ventricles compared to wt littermates. However, PROTOLLIN treatment prevented a pathological enlargement of the lateral ventricles size, which may correlate with hippocampal-brain volume loss. The apparent diffusion coefficient (ADC) of tissue water is found to be highly sensitive for detection of chronic inflammatory processes and edema (Ito et al. J Neurosurg. 1996; 84:97-103). It was found that a reduction in ADC is associated with brain tissue following stroke (Kucinski et al. Stroke. 2002; 33:1786-1791). In our study, we found a decrease in ADC values in transgenic mice that was restore to normal following protollin treatment. Most of the observed changes, by the ADC-map visualization, were in the hippocampal region (data not shown). Hence, PROTOLLIN prevents edema and preserves the brain tissue.

The development of dementia in several neurodegenerative diseases has been shown to correlate with impairment of the cerebrovascular system and in these cases has been defined as vascular dementia. Cognitive impairment has been observed in both familial (Grabowski et al. Ann Neurol. 2001; 49:697-705) and sporadic (Greenberg et al. Neurology. 1993; 43:2073-2079) instances of severe CAA. These observations suggest that CAA can cause clinically important vascular dysfunction (Greenberg et al. Stroke. 35:2616-2619 (2004)). As shown herein, as a result of an accumulation of amyloid in the cerebrovascular vessels of 16month-old TGF-β1 mice those mice suffer from a deficiency in memory and learning. Furthermore, our data shows that PROTOLLIN improves the impairment of recognition memory.

Synaptophysin is a specific component of the membrane of presynaptic vesicles, and possibly important for the biogenesis of synaptic vesicles, vesicle budding, and endocytosis (Daly et al. Proc Natl Acad Sci USA. 2000; 97:6120-6125; Tartaglia et al. J Biol Chem. 2001; 276:37585-37593). In the present study, we reported a remarkable decrease in hippocampal synaptophysin protein expression in 16-month-old TGF-β1 mice as compare to wt littermates. Our result supports previous reports of reduced synaptophysin expression in AD brains (Heffernan et al. Exp Neurol. 1998; 150:235-239). PROTOLLIN administration leads to an increase in hippocampal synaptophysin that is important to hippocampal synaptic plasticity and cognition. Another candidate factor that may regulate neuroplasticity is BDNF in multiple brain regions (Gomez-Pinilla et al. J Neurophysiol. 2002; 88:2187-2195). BDNF is known to improve memory and also regulate synaptic transmission and plasticity in the CNS (Suzuki et al. J Cell Biol. 2004; 167:1205-1215). Furthermore, BDNF is decreased within the brains, serum, and CSF of patients with mild cognitive impairment and AD and can even correlate with Mini Mental State Examination scores (Laske et al. J Neural Transm. 2006; 113:1217-1224). In the PROTOLLIN treated group, BDNF level increased in the hippocampus and was positively correlated with synaptophysin values. Indeed, it was previously shown that BDNF rapidly (within 2 h) upregulates levels of synaptophysin in cerebellar granule cells (Coffey et al. Neurosci Lett. 1997; 227:177-180) and modulates the levels of the vesicle proteins (synaptobrevin and synaptophysin) at the hippocampus synapses (Lu et al. J Neurosci Res. 1999; 58:76-87).

Abnormal deposition of Aβ (1-40), such as in amyloid angiopathy (Leblanc et al. Neurosurgery. 1992; 31:586-590) and certain related disorders including hereditary cerebral hemorrhage amyloidosis-Dutch type (HCHWA-D) (Bornebroek et al. Brain Pathol. 1996; 6:111-114) leads to the degeneration of vascular smooth muscle cells of the large penetrating vessels as well as the cerebral capillaries that represent the BBB (Prior et al. Neuroreport. 1996; 7:562-564) and results in cerebrovascular hemorrhage (Winkler et al. J Neurosci. 2001; 21:1619-1627). A progressive shift of Aβ from soluble to insoluble forms is evident in brains of patients with AD (Wang et al. Exp Neurol. 1999; 158:328-337). In our study, we found that an increase in the production of endogenous Aβ (1-40) in 16-month-old TGF-β1 mice, correlated to the presence of vascular and meningeal Congo red reactivity. A decrease of insoluble Aβ (1-40) and an increase of brain and plasma soluble Aβ (140) following PROTOLLIN treatment, raises a possibility that the insoluble Aβ is converted to a soluble form by Aβ degrading enzymes and then transferred to the plasma. Conversion of Aβ from insoluble to soluble forms by PROTOLLIN may facilitate the removal of Aβ from the brain and explain the improved performance of the TGFβ1 mice when cognitively tested.

Recently, it was reported a physiological role of macrophages in the regulation and clearing of cerebrovascular amyloid in AD mice (Hawkes et al. Proc Natl Acad Sci USA. 2009; 106:1261-1266). We showed that activated macrophage cells were present around amyloid depositions in PROTOLLIN treated mouse brains and this activation is associated with a reduction in CAA pathology. In addition, we found a significantly increased expression of monocyte activation markers, such as TNFα and CD11b, in the blood of PROTOLLIN-treated mice. These results are in agreement with those of an earlier studies (Frenkel et al. Ann Neurol. 2008; 63:591-601; Frenkel et al. J Clin Invest. 2005; 115:2423-2433) showing that nasal PROTOLLIN, in an AD mouse model, activates microglia or macrophage cells to clear amyloid.

It was previously suggested that a defect in IDE activity contributes to the accumulation of amyloid in the cortical microvasculature (Morelli et al. J Biol Chem. 2004; 279: 56004-56013). Furthermore, activity of IDE was significantly reduced in CAA as compared with age-matched controls (Morelli et al. J Biol Chem. 2004; 279:56004-56013). We found an upregulation of IDE in the peritoneal macrophages after nasal PROTOLLIN.

Furthermore, there was an increase of CCR2 in peritoneal macrophages after nasal PROTOLLIN. CCR2 is a chemokine receptor expressed on microglia, which mediates the accumulation of mononuclear phagocytes at sites of inflammation. CCR2 is also required for the migration of CD11b+ cells into the brain.

In summary, our study demonstrates that activation of macrophages by nasal PROTOLLIN is a novel therapeutic approach to reduce microhemorrhage, prevent stroke and improve cognition in a model of cerebral amyloid angiopathy.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating Cerebral Amyloid Angiopathy (CAA) in a subject, the method comprising:
identifying a subject who has been diagnosed with CAA but who has not been diagnosed with Alzheimer's Disease;
selecting the subject on the basis that they have CAA; and
nasally administering a therapeutically effective amount of a proteosome-based adjuvant to the identified subject.

2. The method of claim 1, further comprising diagnosing the subject with CAA.

3. The method of claim 2, wherein the diagnosis of CAA is made according to the Boston Cerebral Amyloid Angiopathy Group guidelines.

4. The method of claim 2, wherein the diagnosis is made based on the presence of a single lobar, cortical, or cortico-subcortical hemorrhage without another cause, multiple hemorrhages with a possible but not a definite cause, or a hemorrhage in an atypical location.

5. The method of claim 1, further comprising administering one or more clinical tests to evaluate the effectiveness of the treatment.

6. The method of claim 5, wherein the clinical tests include one or more imaging studies.

7. The method of claim 5, wherein the clinical tests include a cognitive evaluation.

8. The method of claim 1, further comprising administering one or more treatments for CAA.

9. The method of claim 8, wherein the one or more treatments include surgical hematoma evacuation, or administration of a pharmaceutical.

10. A method of decreasing risk of recurrence of intracranial hemorrhage (ICH) in a subject who has had at least one diagnosed ICH and who has not been diagnosed with Alzheimer's Disease, the method comprising: identifying a subject who has had at least one diagnosed ICH, and nasally administering a therapeutically effective amount of a proteosome-based adjuvant to the identified subject.

11. The method of claim 9, wherein the pharmaceutical is a corticosteroid or cyclophosphamide.

* * * * *

UNITED STATES PATENT AND TRADEMARK OFFICE
CERTIFICATE OF CORRECTION

PATENT NO. : 9,757,448 B2
APPLICATION NO. : 13/579817
DATED : September 12, 2017
INVENTOR(S) : Howard Weiner, Dan Frenkel and Veronica Lifshitz Page 1 of 1

It is certified that error appears in the above-identified patent and that said Letters Patent is hereby corrected as shown below:

On the Title Page

Column 2 (Other Publication), Line 32, delete "Ageining" and insert -- Ageing --;

Column 2 (Other Publication), Line 38, delete "Proteosome" and insert -- Proteasome --;

Column 2 (Other Publication), Line 40, delete "proteosome-based" and insert -- proteasome-based --;

Column 2 (Abstract), Lines 2-3, delete "Proteosome" and insert -- Proteasome --;

In the Claims

In Column 16, Line 25 (approx.), in Claim 1, delete "proteosome-based" and insert -- proteasome-based --;

In Column 16, Lines 54-55 (approx.), in Claim 10, delete "proteosome-based" and insert -- proteasome-based --.

Signed and Sealed this
Twenty-fourth Day of April, 2018

Andrei Iancu
*Director of the United States Patent and Trademark Office*